(12) United States Patent
Megerian et al.

(10) Patent No.: US 11,204,691 B2
(45) Date of Patent: Dec. 21, 2021

(54) REDUCING INPUT REQUESTS IN RESPONSE TO LEARNED USER PREFERENCES

(71) Applicant: International Business Machines Corporation, Armonk, NY (US)

(72) Inventors: Mark Gregory Megerian, Rochester, MN (US); Thomas J Eggebraaten, Rochester, MN (US); Marie Louise Setnes, Bloomington, MN (US); John Petri, St. Charles, MN (US); Adam Clark, Mantorville, MN (US)

(73) Assignee: International Business Machines Corporation, Armonk, NY (US)

( * ) Notice: Subject to any disclaimer, the term of this patent is extended or adjusted under 35 U.S.C. 154(b) by 4 days.

(21) Appl. No.: 16/268,016

(22) Filed: Feb. 5, 2019

(65) Prior Publication Data
US 2020/0249826 A1 Aug. 6, 2020

(51) Int. Cl.
*G06F 3/0484* (2013.01)
*G06F 3/0482* (2013.01)
*G06N 20/00* (2019.01)

(52) U.S. Cl.
CPC ........ *G06F 3/04847* (2013.01); *G06F 3/0482* (2013.01); *G06N 20/00* (2019.01)

(58) Field of Classification Search
CPC .... G06F 3/048; G06F 3/04847; G06F 3/0482; G06N 20/20; G06N 5/04–048; G16H 50/20; G06Q 10/08; G06Q 50/28–32; G06Q 10/063
See application file for complete search history.

(56) References Cited

U.S. PATENT DOCUMENTS

| 8,346,681 B2 * | 1/2013 | Lauritsen ............... G06N 5/042 706/11 |
| 2004/0119755 A1 * | 6/2004 | Guibourge .......... H04M 1/2745 715/827 |
| 2012/0036128 A1 | 2/2012 | Kenedy et al. |

(Continued)

OTHER PUBLICATIONS

"Hayes, Conor, Pádraig Cunningham, and Michelle Doyle. ""Distributed cbr using xml."" Proceedings of the KI-98 Workshop on Intelligent Systems and Electronic Commerce. 1998. "(Year: 1998).*

*Primary Examiner* — Liang Y Li
(74) *Attorney, Agent, or Firm* — Patterson + Sheridan, LLP

(57) ABSTRACT

Embodiments provide for reduced user input requests by identifying predefined diagnosis paradigms; creating a synthetic diagnosis paradigm via a machine learning process based on prior selections of action plans recommended by the predefined diagnosis paradigms and values entered therefor, wherein the synthetic diagnosis paradigm identifies the action plans to treat the plurality of conditions based on a subset of the attribute inputs used by the predefined diagnosis paradigms; generating a graphical user interface (GUI) to prompt input for values for the subset of attribute inputs; in response to receiving the values for the subset of attribute inputs, identifying at least one condition according to the predefined and synthetic diagnosis paradigms; and displaying the action plans in the GUI in association with the synthetic and predefined diagnosis paradigms according to evaluations of the action plans based on the respective logical structures.

20 Claims, 8 Drawing Sheets

(56) References Cited

U.S. PATENT DOCUMENTS

| | | | |
|---|---|---|---|
| 2012/0047105 A1 | 2/2012 | Saigal et al. | |
| 2013/0035912 A1* | 2/2013 | Margines | G06N 7/00 703/2 |
| 2013/0151383 A1* | 6/2013 | Gancarz | G06Q 40/02 705/30 |
| 2014/0358828 A1* | 12/2014 | Phillipps | G06N 20/20 706/12 |
| 2016/0055302 A1* | 2/2016 | Sellars | G16Z 99/00 705/3 |
| 2017/0076046 A1 | 3/2017 | Barnes et al. | |
| 2018/0322402 A1* | 11/2018 | Kulkarni | G06N 3/006 |
| 2018/0366222 A1* | 12/2018 | Tang et al. | G16H 50/20 |
| 2019/0005199 A1* | 1/2019 | Rowley Grant et al. | G16H 40/63 |
| 2019/0108313 A1* | 4/2019 | Jarrett | G16H 10/60 |
| 2019/0108470 A1* | 4/2019 | Jain | G06Q 10/063118 |

* cited by examiner

| | Paradigm A | Paradigm B | Paradigm C |
|---|---|---|---|
| Attribute 1 | request 230a | request 230f | request 230k |
| Attribute 2 | request 230b | optional 230g | request 230l |
| Attribute 3 | request 230c | not used 230h | optional 230m |
| Attribute 4 | optional 230d | request 230i | request 230n |
| Attribute 5 | request 230e | request 230j | not used 230o |

FIG. 2A

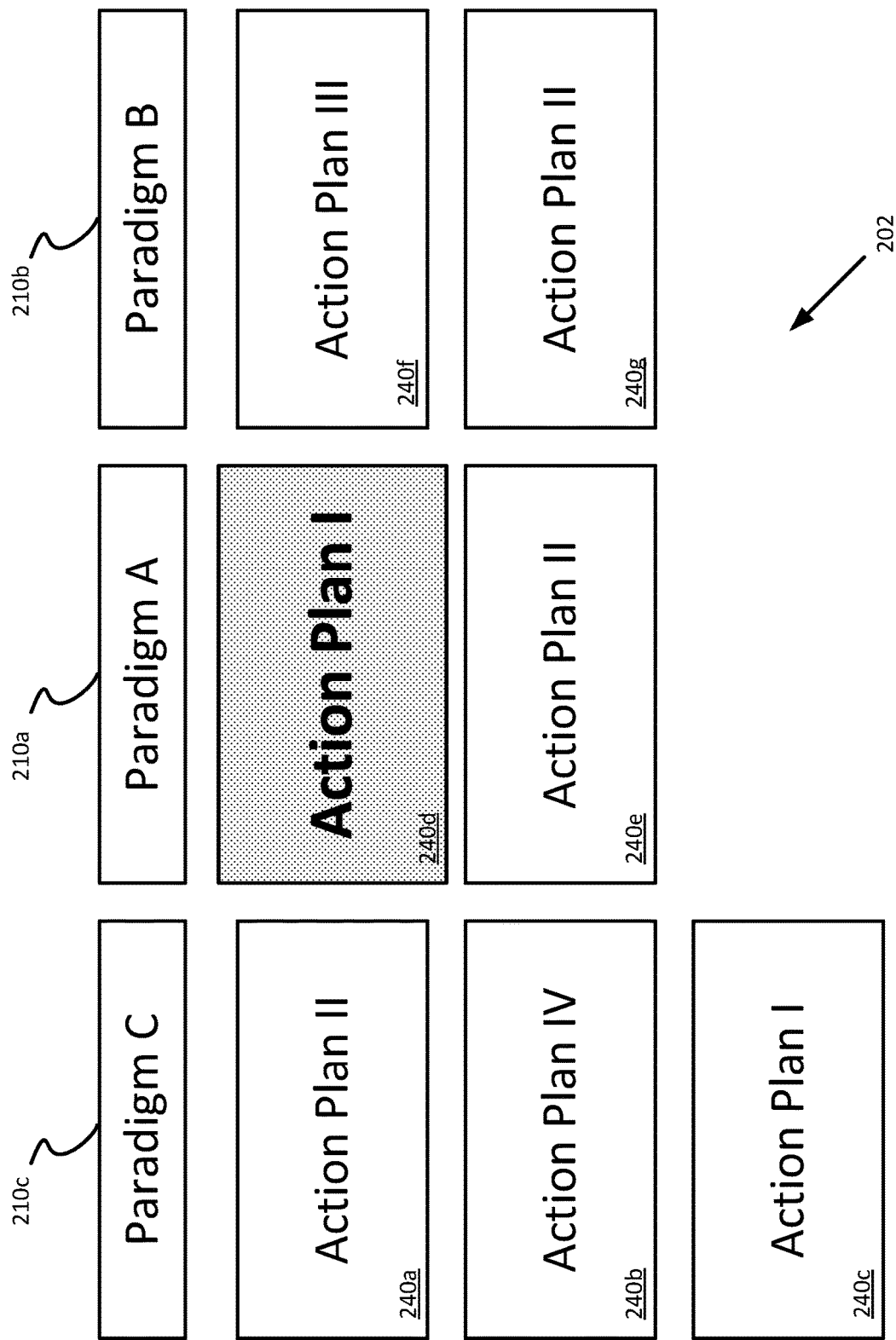

REDUCING INPUT REQUESTS IN RESPONSE TO LEARNED USER PREFERENCES

BACKGROUND

The present invention relates to Graphical User Interfaces (GUI), and more specifically, to improving the functionality of how the GUI presents information to a user and requests input from a user. Various designers of GUIs may select which elements of those GUIs to emphasize, or allow users to select which elements to emphasize (e.g., via dialog boxes). Similarly, various designers of GUIs may present requests for inputs, and allow users to autofill various fields.

SUMMARY

According to one embodiment of the present invention, reducing input requests in response to learned user preferences is provided via a method that includes identifying a plurality of predefined diagnosis paradigms that identify candidate action plans to treat a plurality of conditions, wherein each predefined diagnosis paradigm includes a logical structure that evaluates which conditions of the plurality of conditions to treat by which of the candidate action plans based on attribute inputs; creating a synthetic diagnosis paradigm via a machine learning process based on prior selections of the candidate action plans from the plurality of diagnosis paradigms and values entered for the attribute inputs on the prior selections of the candidate action plans, wherein the synthetic diagnosis paradigm identifies the candidate action plans to treat the plurality of conditions based on a subset of the attribute inputs used by the plurality of predefined diagnosis paradigms and includes a synthetic logical structure that evaluates which conditions of the plurality of conditions to treat; generating a graphical user interface (GUI) to prompt input for values for the subset of attribute inputs; in response to receiving the values for the subset of attribute inputs, identifying at least one condition of the plurality of conditions according to the plurality of predefined diagnosis paradigms and the synthetic diagnosis paradigm; and displaying the candidate action plans in the GUI in association with the synthetic diagnosis paradigm and the plurality of predefined diagnosis paradigms according to evaluations of the candidate action plans based on respective logical structures for the plurality of predefined diagnosis paradigms and the synthetic diagnosis paradigm.

According to one embodiment of the present invention, reducing input requests in response to learned user preferences is provided via a system that includes a processor; and a memory storage device including instructions that when performed by the processor cause the system to: identify a plurality of predefined diagnosis paradigms that identify candidate action plans to treat a plurality of conditions, wherein each predefined diagnosis paradigm includes a logical structure that evaluates which conditions of the plurality of conditions to treat by which of the candidate action plans based on attribute inputs; create a synthetic diagnosis paradigm via a machine learning process based on prior selections of the candidate action plans from the plurality of diagnosis paradigms and values entered for the attribute inputs on the prior selections of the candidate action plans, wherein the synthetic diagnosis paradigm identifies the candidate action plans to treat the plurality of conditions based on a subset of the attribute inputs used by the plurality of predefined diagnosis paradigms and includes a synthetic logical structure that evaluates which conditions of the plurality of conditions to treat; generate a graphical user interface (GUI) to prompt input for values for the subset of attribute inputs; in response to receiving the values for the subset of attribute inputs, identify at least one condition of the plurality of conditions according to the plurality of predefined diagnosis paradigms and the synthetic diagnosis paradigm; and display the candidate action plans in the GUI in association with the synthetic diagnosis paradigm and the plurality of predefined diagnosis paradigms according to evaluations of the candidate action plans based on respective logical structures for the plurality of predefined diagnosis paradigms and the synthetic diagnosis paradigm.

According to one embodiment of the present invention, reducing input requests in response to learned user preferences is provided via a computer readable storage medium including instructions that when performed by a processor configure the processor to: identify a plurality of predefined diagnosis paradigms that identify candidate action plans to treat a plurality of conditions, wherein each predefined diagnosis paradigm includes a logical structure that evaluates which conditions of the plurality of conditions to treat by which of the candidate action plans based on attribute inputs; create a synthetic diagnosis paradigm via a machine learning process based on prior selections of the candidate action plans from the plurality of diagnosis paradigms and values entered for the attribute inputs on the prior selections of the candidate action plans, wherein the synthetic diagnosis paradigm identifies the candidate action plans to treat the plurality of conditions based on a subset of the attribute inputs used by the plurality of predefined diagnosis paradigms and includes a synthetic logical structure that evaluates which conditions of the plurality of conditions to treat; generate a graphical user interface (GUI) to prompt input for values for the subset of attribute inputs; in response to receiving the values for the subset of attribute inputs, identify at least one condition of the plurality of conditions according to the plurality of predefined diagnosis paradigms and the synthetic diagnosis paradigm; and display the candidate action plans in the GUI in association with the synthetic diagnosis paradigm and the plurality of predefined diagnosis paradigms according to evaluations of the candidate action plans based on respective logical structures for the plurality of predefined diagnosis paradigms and the synthetic diagnosis paradigm.

BRIEF DESCRIPTION OF THE SEVERAL VIEWS OF THE DRAWINGS

FIGS. 2A-2E illustrate the operations of reducing input requests in a Graphical User Interface, according to aspects of the present disclosure.

DETAILED DESCRIPTION

Figure 1:
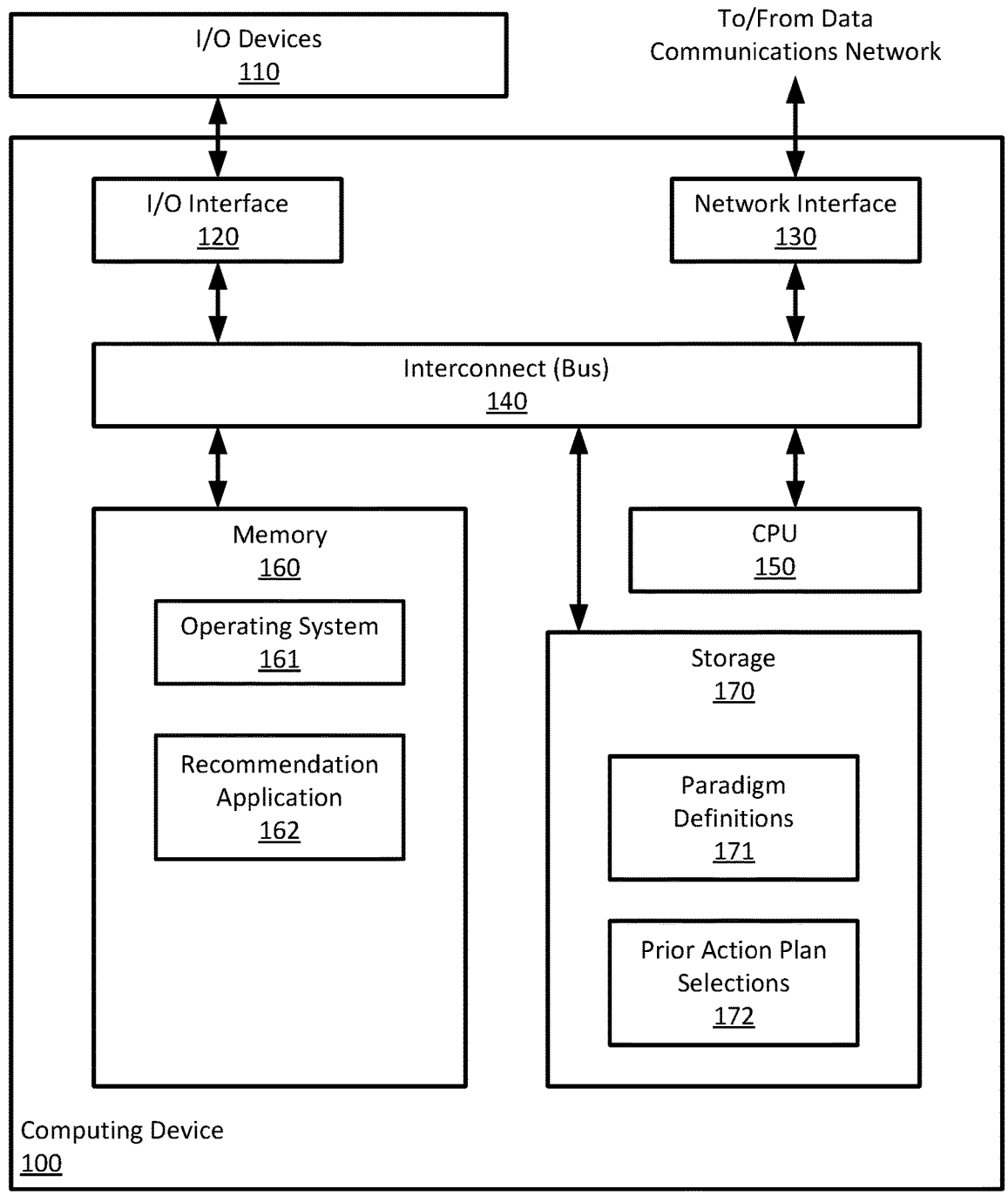
FIG. 1 illustrates a computing system, according to aspects of the present disclosure.

Various Graphical User Interfaces (GUI) may be presented in various formats to present ranked options that users may select from. As discussed herein, a paradigm (also referred to as a diagnosis paradigm) is a logical structure that is used to identify a condition (or several conditions) that may be addressed by one or more action plans. The paradigms provide rankings for the various actions plans and identify which actions plans are to be displayed in a GUI and what order those actions plans are to be presented in. For example, a maintenance technician may be presented with a GUI that shows several action plans for troubleshooting a nonconformance in a device or structure (e.g., an air conditioner, a building, a computer, a vehicle) and several paradigms (e.g., a manufacturer's recommendation, a company policy, previous technician's notes) that recommend one action plan over another action plan. In another example, a healthcare professional may be presented with a GUI that shows several actions plans for treating a condition in a patient and several paradigms (e.g., Hospital policy, National Code, Previous treatment plans, research notes) that recommend one action plan over another action plan. Similarly, the various paradigms may be ranked so that a mandated or more-trusted paradigm is presented with greater prominence in the GUI.

The paradigms determine which conditions are likely and the recommended action plans to address the determined conditions based on various attribute inputs received from users. A user may provide inputs that help identify the condition afflicting an entity and the paradigms can use the provided attribute inputs to provide a ranked list of preferred action plans to address the identified conditions. For example, a maintenance technician may be prompted for various temperatures, pressures, voltages, thicknesses, etc. to identify a condition affecting a device or structure, and the several paradigms accordingly provide recommendations to treat, solve, ameliorate, or otherwise address those conditions. The recommended action plans may be ranked according to the individual paradigms used to evaluate how to address the identified condition(s), and are not necessarily the same between paradigms.

When evaluating the action plans of multiple paradigms in parallel, a user may be presented with requests for attributes that are used in one paradigm, but not another paradigm, or the requests may omit prompts for attributes needed by one paradigm to properly evaluate what condition to address. These prompting strategies may negatively affect the user experience or effectiveness of evaluating multiple paradigms in parallel by requiring excessive data entry or providing insufficient data to accurately provide recommendations. The present disclosure provides for the synthesis of several predefined paradigms into a synthetic diagnosis paradigm that uses a machine-learning curated subset of attribute inputs to identify conditions and recommend action plans to address those conditions. As action plans are selected from the GUI, the machine learning model may update the GUI and the synthetic paradigm to learn and adapt to the user's preferences and identify the most influential attributes to request from a user. Because the user is prompted for fewer, but more relevant, attribute input values, the synthetic diagnosis paradigm may improve the user experience and thereby improve the functionality of the computer device used to provide the GUI with the action plans.

FIG. 1 illustrates a computing system 100, which may be a personal computer, a laptop, a tablet, a smartphone, etc. As shown, the computing system 100 includes, without limitation, a central processing unit (CPU) 150, a network interface 130, an interconnect 140, a memory 160, and storage 170. The computing system 100 may also include an I/O device interface 120 connecting I/O devices 110 (e.g., keyboard, display and mouse devices) to the computing system 100.

The CPU 150 retrieves and executes programming instructions stored in the memory 160. Similarly, the CPU 150 stores and retrieves application data residing in the memory 160. The interconnect 140 facilitates transmission, such as of programming instructions and application data, between the CPU 150, I/O device interface 120, storage 170, network interface 140, and memory 160. CPU 150 is included to be representative of a single CPU, multiple CPUs, a single CPU having multiple processing cores, and the like. And the memory 160 is generally included to be representative of a random access memory. The storage 170 may be a disk drive storage device. Although shown as a single unit, the storage 170 may be a combination of fixed and/or removable storage devices, such as magnetic disk drives, flash drives, removable memory cards or optical storage, network attached storage (NAS), or a storage area-network (SAN). The storage 170 may include both local storage devices and remote storage devices accessible via the network interface 130.

Further, computing system 100 is included to be representative of a physical computing system as well as virtual machine instances hosted on a set of underlying physical computing systems. Further still, although shown as a single computing system, one of ordinary skill in the art will recognized that the components of the computing system 100 shown in FIG. 1 may be distributed across multiple computing systems connected by a data communications network.

As shown, the memory 160 includes an operating system 161 (e.g., Microsoft's WINDOWS® Operating System) and a recommendation application 162. The recommendation application 162 accesses one or more paradigm definitions 171 to determine which action plans to recommend to a user under a particular paradigm. The paradigm definitions 171 include a logical structure used to evaluate which action plans are to be recommended under certain conditions according to a respective diagnosis paradigm, and the recommendation application 162 evaluates several diagnosis paradigms in parallel. Depending on the logical structures of the paradigms, various action plans may be ranked higher or lower in different diagnosis paradigms, and the recommendation application 162 may display the recommendations according to the paradigm-specific scores in a GUI.

As attribute inputs and selections of action plans from the GUI are received over time from various users, a corpus 172 of prior recommendations and action plan selections is collected. The recommendation application 162 identifies which action plans are historically selected, by whom, and how often the user(s) selected the action plans (i.e., a frequency of selection). Using the corpus 172, the recommendation application 162 learns the user preferences for action plans from the corpus 172 on what attributes the users have historically input when selecting between action plans or identifying conditions to address by the action plans.

The recommendation application 162, synthesizes a paradigm from the historic data and the predefined paradigms in the memory 160. The paradigm synthesized by the recommendation application 162 may be referred to as a preferred paradigm or a synthetic paradigm, and the recommendation application 162 may display the synthetic paradigm in the GUI with recommendations from the predefined paradigms, or may use the synthetic paradigm to identify attributes to request values for, which are then fed into the predefined paradigms to evaluate and choose action plans to display in the GUI.

For example, a recommendation application 162 may identify and receive predefined paradigms from a hospital system, a first national healthcare bureau, a second national healthcare bureau (e.g., from a different country than the first), and a research institution. Each of the predefined paradigms may rank different various actions plans for the same condition differently; placing emphasis on different aspects of the action plans to identify a "best" action plan of those available. Similarly, the predefined paradigms may each request different data related to attributes for a patient (or other treated entity) in selecting a treatment as an action plan. The recommendation application 162, via a machine learning process, identifies which attributes are useful in differentiating action plans and identifies which action plans are selected over time. Using the historic selection data, the recommendation application creates the synthetic paradigm to request/use a subset of the attribute inputs that are most-useful in identifying a preferred action plan.

FIG. 2A illustrates a data table 200 that shows a relationship between how various paradigms 210a-c (generally, paradigm 210) use various attribute inputs 220a-e (generally, attribute inputs 220). A particular attribute input 220 may have a status 230 (individually, statuses 230a-o) that indicates that the attribute input 210 is requested/used by a particular paradigm 210, not request/used by a particular paradigm 210, or is optionally or occasionally used/requested by a particular paradigm 210. In the following examples, paradigm C 210c is a synthetic paradigm; synthesized from the predefined paradigms of paradigm A 210a and paradigm B 210b, based on the historic selection data. As such, the statuses 230k-o for how Paradigm C 210c uses the attributes 220a-e are derived from the statuses of 230a-e and 230f-j from paradigm A 210a and paradigm B 210b respectively.

The machine learning process identifies which attributes the recommendation application 162 can omit from requesting with minimal effect on the recommended action plans under the paradigms 210. As illustrated in FIG. 2A, although Paradigm A 210a and Paradigm B 210b both require the input of a fifth attribute 220e, the synthetic paradigm C 210c does not use the fifth attribute 220e. In some embodiments, the machine learning process identifies that the fifth attribute 220e can be omitted based on historic data showing that the value input for the fifth attribute 220e varying in value without affecting the end result action plan recommendation. In some embodiments, the machine learning process identifies that the fifth attribute 220e can be omitted based on historic data showing that the value input for the fifth attribute 220e rarely varies and may be replaced with an automatic entry of a most-frequent or average historic value without affecting the end result action plan recommendation. In some embodiments, the machine learning process identifies that the fifth attribute 220e can be optionally omitted based on historic data showing that the value input for the fifth attribute 220e only has an effect on the end result action plan for certain values of another attribute (e.g., when a first attribute 220a is true, the fifth attribute 220e can be omitted, but when the first attribute 220a is false, the fifth attribute 220e should be requested).

Figure 2B:
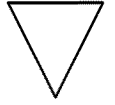

Turning now to FIG. 2B, a GUI for a request dialog 201 is shown based on the attribute input requirements determined according to the synthetic paradigm C 220c from FIG. 2A. The request dialog 201 may include various user input controls (e.g., radio buttons, check boxes, text boxes, drop down menus, sliders, dials, buttons, etc.) to accept the requested attribute inputs from a user. The particular user input controls and arrangement thereof varies in different embodiments based on the preferred diagnosis paradigm 210, and which attributes 220 are required, optional, or omitted from being requested or used thereby. Although the preferred paradigm in the current examples is presented as the synthetic paradigm C 210c, in other embodiments, a user may select a predefined paradigm to use as the preferred paradigm.

Based on the values received from the request dialog 201, the recommendation application 162 generates a GUI 202 to display various recommended action plan indicators 240a-g (generally, action plan indicator 240) that a user may select to choose an action plan. In various embodiments, the order of the indicators for the paradigms 210 are arranged according to learned user preferences for the individual paradigms 210 to present the more-preferred paradigms 210 in more prominent positions/arrangements in the GUI 202 than less-preferred paradigms 210. The order of the individual action plan indicators 240 is determined based on how the logical structures of the associated paradigms 210 score/rank the individual action plans so that the more-preferred action plans are displayed in more prominent positions/arrangements in the GUI 202 than less-preferred paradigms 210.

Figure 2C:
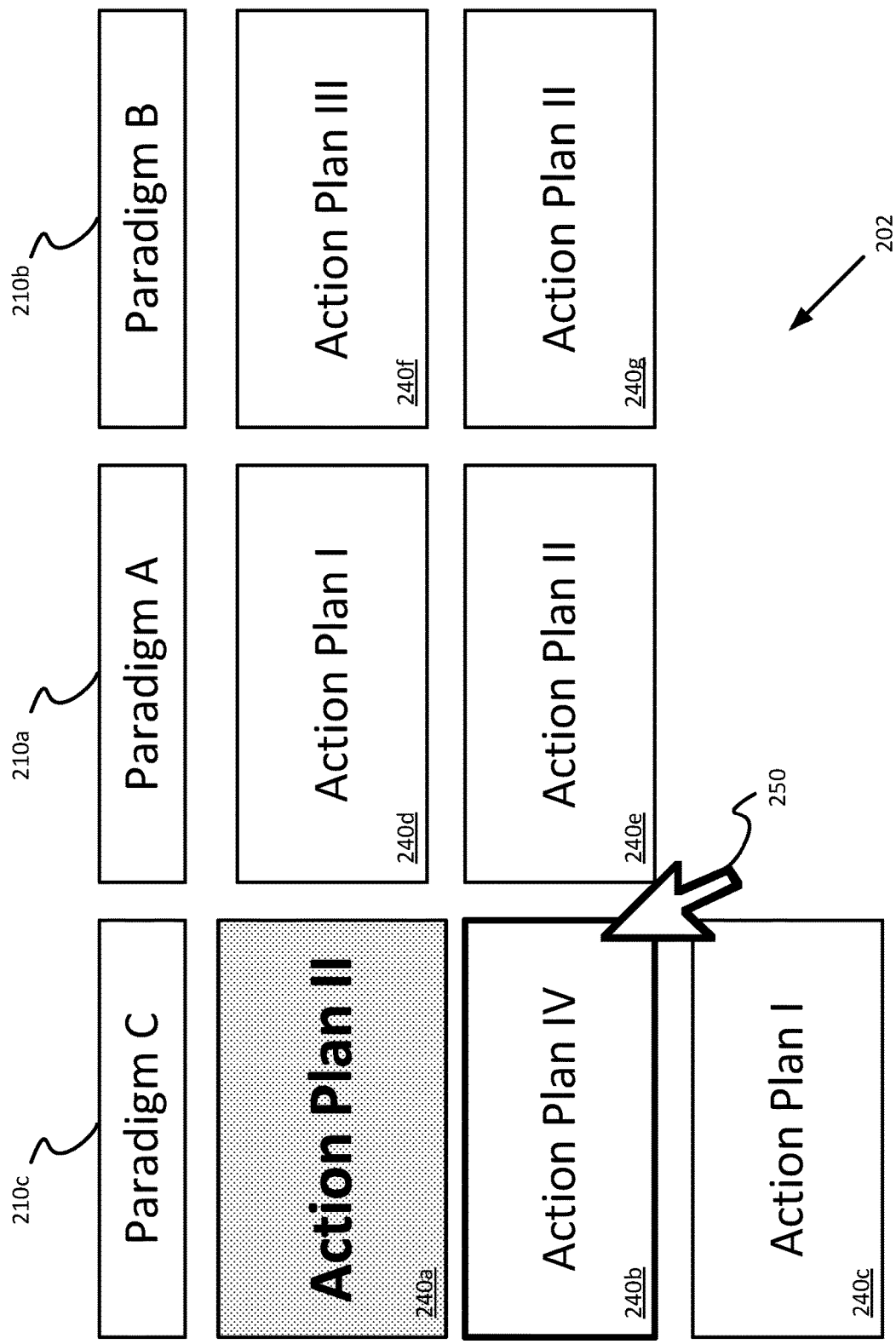

In the example illustrated in FIG. 2C, paradigm C 210c is displayed in a most-prominent position (e.g., for a user using a language read from left-to-right, this may be a top left position in a the GUI 202), and action plan II is displayed in the most prominent position in relation to the indicator for paradigm C 210c to indicate that action plan II (associated with the first action plan indicator 240a) is the recommended or preferred action plan according to paradigm C 210c. In some embodiments, the recommendation application 162 also highlights the action plan indicator 240 for the preferred action plan via different coloration or sizing than non-preferred action plans. The user may select one of the action plans via a cursor 250, keyboard command, touch gesture, etc., which in the example illustrated in FIG. 2C is not the preferred action plan (associated with the first action plan indicator 240a), but action plan IV, which is associated with the second action plan indicator 240b.

Figure 2D:
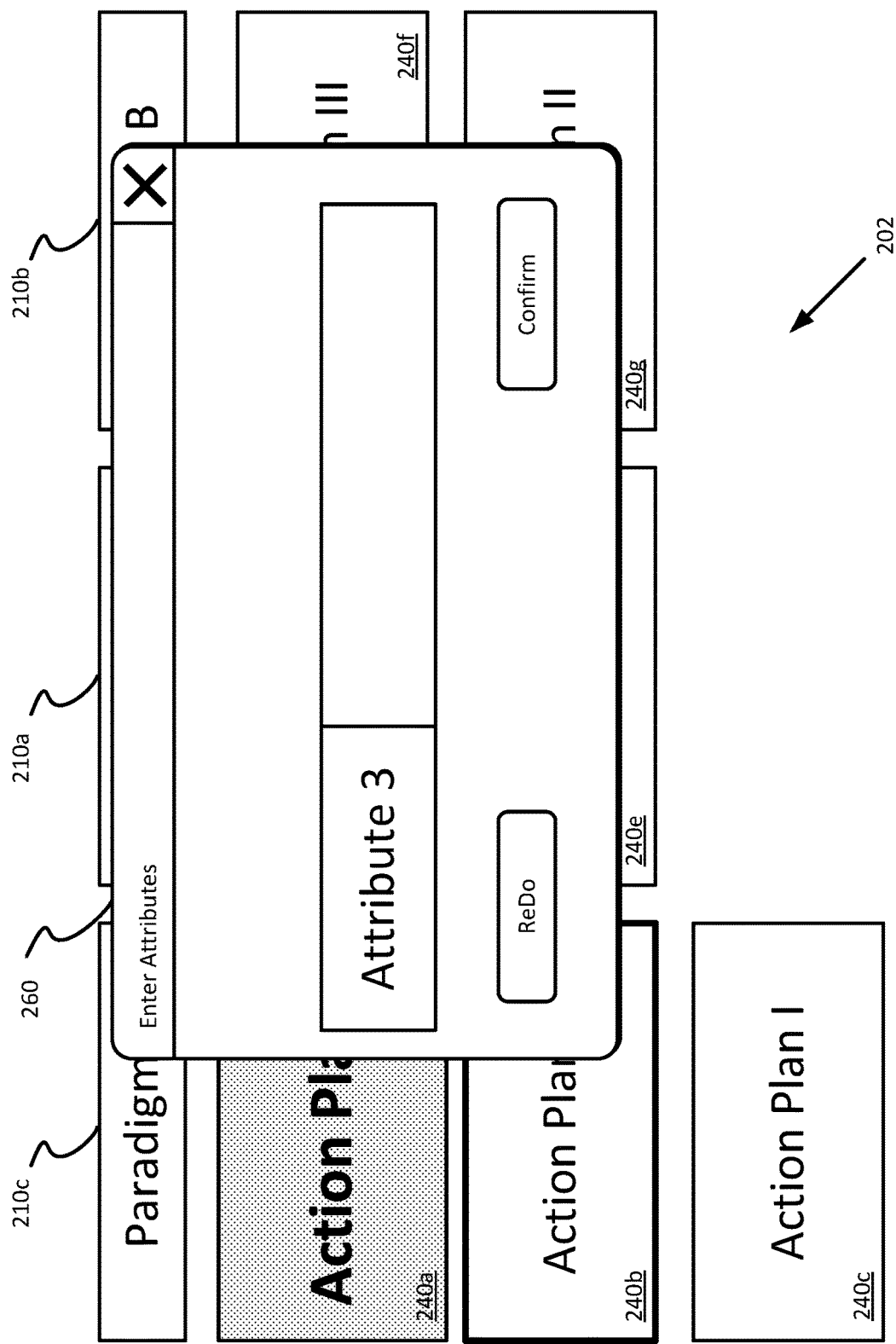

In response to receiving a selection in the GUI of a non-preferred action plan, the recommendation application 162 may display a dialog box 260, such as illustrated in FIG. 2D, to prompt the user for additional attribute inputs (e.g., for an attribute identified as optional or not required), or prompt the user for a reason why a non-preferred action plan was selected instead of the preferred action plan.

In response to receiving the additional input from the dialog box 260, the recommendation application 162 may reevaluate which action plan to recommend based on newly received attribute data. In various embodiments, the newly preferred action plan may be the action plan selected by the user. In some embodiments, such as is illustrated in FIG. 2E, the newly preferred action plan may be a different action plan that that previously selected by the user.

Figure 3:
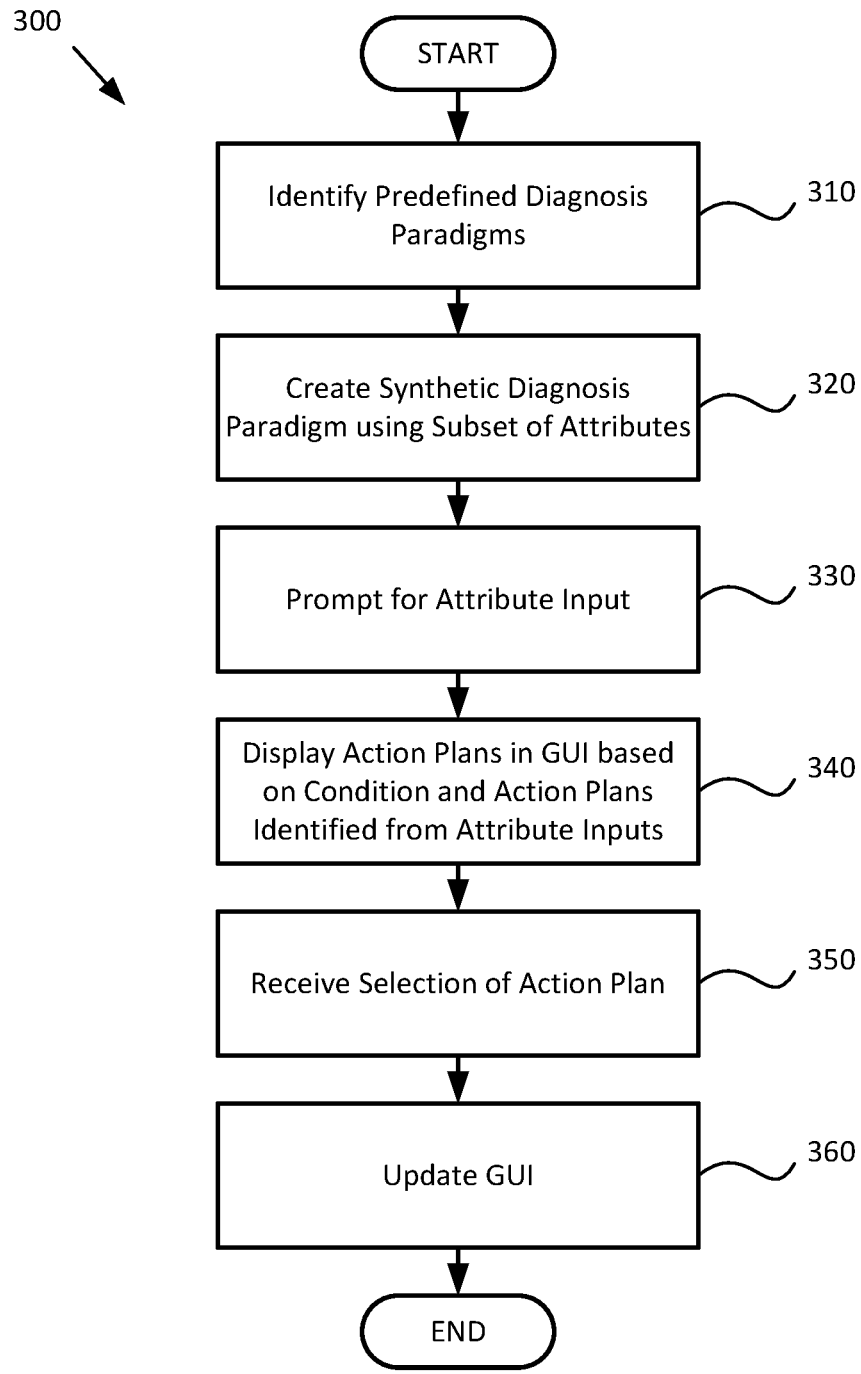
FIG. 3 is a flowchart of a method to reduce input requests in response to learned user preferences, according to aspects of the present disclosure.

FIG. 3 is a flowchart of a method 300 to reduce input requests in response to learned user preferences. Method 300 begins with block 310, where the recommendation application 162 identifies a plurality of predefined diagnosis paradigms that identify candidate action plans to treat one or more conditions for an entity. For example, several diagnosis paradigms may be identified to correct technical non-conformance conditions in a product (e.g., a manufacturer's recommendation plan, a maintenance department manual) or medical conditions in an entity (e.g., a national health code, a hospital procedure guideline). The predefined diagnosis paradigm includes a logical structure included in a paradigm definition 171 that evaluates which candidate action plans to recommend addressing an identified condition based on one or more attribute inputs that a user provides during troubleshooting or condition diagnosis. As part of the troubleshooting or condition diagnosis process, the recommendation application 162 monitors the selections of action plans made by the user, and the attributes input into the recommendation application 162 that lead to those selections so that a corpus 172 of historic data is generated.

At block 320, the recommendation application 162 creates a synthetic diagnosis paradigm via a machine learning process based on the corpus 172 of historic data (e.g., prior selections of candidate action plans and values entered for the attribute inputs on the prior selections of the candidate action plans). The recommendation application 162, via the machine learning process, identifies which attributes of the several attributes used by the several predefined paradigms have the most significant effects on the action plans chosen by the user, and creates the synthetic diagnosis paradigm to identify the candidate action plans by using that subset of the attributes. The recommendation application 162 selects the particular attribute inputs that make up the subset of attribute inputs from the plurality of attribute inputs used in the predefined paradigms based on an impact ranking that identifies which of the attribute inputs most strongly differentiate between conditions of the plurality of conditions or action plans of the plurality of action plans. For example, if an attribute of "age" or "days since last service" used in one or more predefined paradigms is identified as having little impact on which options are recommended (e.g., the recommendation application 162 consistently identifies the same conditions or action plans regardless of the value provided for that attribute), that attribute may be omitted from the subset used by the synthetic paradigm. The synthetic diagnosis paradigm includes a synthetic logical structure that evaluates the subset of attributes to determine which conditions of the plurality of conditions to address and which action plan to recommend for that treatment.

At block 330, the recommendation application 162 prompts the user for attribute inputs according to the identified subset of attributes. In various embodiments, the recommendation application 162 prompts the user for input by generating a GUI or dialog box in an existing GUI with various fields configured to accept values for the subset of attributes.

At block 340, in response to receiving the values for the subset of attribute inputs (prompted for per block 330), the recommendation application 162 displays various action plans in a GUI that are ranked according to the various predefined and synthetic diagnosis paradigms. The recommendation application 162 may evaluate various action plans according to several ranking schemes (provided by the plurality of paradigms) in parallel for display to a user so that several action plans to address at least one identified condition may be evaluated by the user with regard to the paradigms' evaluations of those action plans. For paradigms that evaluate action plans using attributes not included in the subset prompted for, the recommendation application 162 may automatically use a most-frequently input historic value or use a placeholder value (including a null value).

The GUI may show the ranked recommendations from a first diagnosis standard, a second diagnosis standard, and a third diagnosis standard to allow the user to see what action plans are recommended in common, which action plans are uniquely recommended, and how highly each diagnosis standard recommends a particular action plan before making the user's own evaluation. In various embodiments, the recommendation application 162 may prioritize the display of the various diagnosis paradigms and/or action plans to highlight a preferred action plan, a preferred diagnosis paradigm, or anomalous/unique action plans. The GUI may organize the action plans based on the rankings provided by one or more paradigms, and may organize the paradigms based on learned or specified user preferences for display.

At block 350, the recommendation application 162 receives a selection of an action plan from the GUI. A user may select an action plan from the GUI by software interfaces (e.g., a mouse and cursor), a keyboard shortcut, voice command, touch command, gesture, or the like. The selection may be made independently of the paradigm that recommends the action plan, or in association with the paradigm recommending the action plan. For example, a GUI that presents Action Plan X in association with several paradigms may receive a selection of Action Plan X from a portion of the GUI associated with one of the several paradigms and treat the selection as being made in association with that particular paradigm. In another example, a GUI that presents Action Plan X in association with several paradigms may receive a selection of Action Plan X via a voice command to select Action Plan X, which is independent of any paradigm under which Action Plan X is recommended, and the recommendation application 162 may treat the independent selection as a selection associated with the preferred paradigm, all of the paradigms recommending Action Plan X, or none of the paradigms in various embodiments.

At block 360, in response to the selection made (per block 360), the recommendation application 162 updates the GUI. In various embodiments, the selection of an action plan moves the recommendation application 162 to a next phase in addressing the condition, and updating the GUI include presenting a new interface for the user to handle the next phase (e.g., step-by-step operations according to the action plan selected). In some embodiments, such as when the action plan was selected from a non-preferred paradigm or as a non-preferred action plan (e.g., an action plan other than the highest recommended action plan for a given paradigm), updating the GUI includes prompting the user for additional data, such as a reason why the selection was made or additional attribute inputs to justify the selection. In other embodiments, when the action plan is selected from a paradigm that uses more attribute inputs than the preferred paradigm, the recommendation application 162 refrains from requesting more inputs; allowing the user to select a recommended action plan without inputting the attributes beyond those in the subset.

Method 300 may then conclude.

Figure 4:
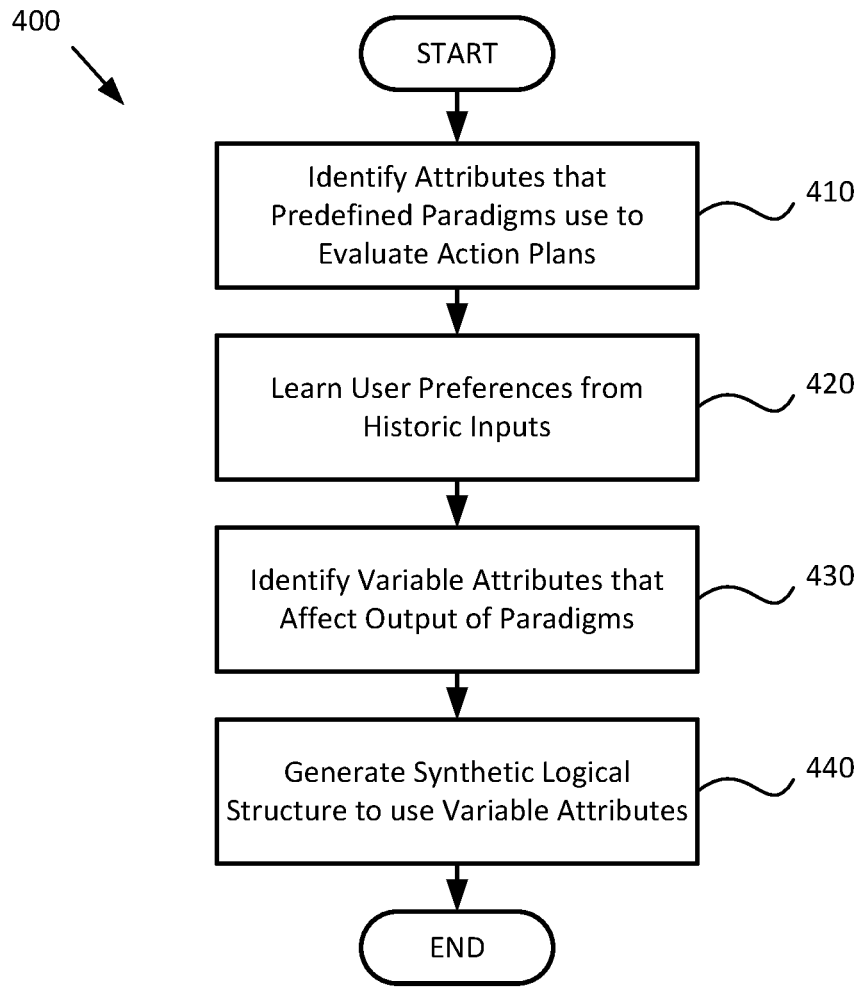
FIG. 4 is a flowchart of a method to synthesize a diagnosis paradigm from predefined diagnosis paradigms and learned user preferences, according to aspects of the present disclosure.

FIG. 4 is a flowchart of a method 400 to synthesize a diagnosis paradigm from predefined diagnosis paradigms and learned user preferences. Method 400 begins with block 410, where the recommendation application 162 identifies the attributes that are requested by several predefined paradigms to evaluate action plans that address various conditions. A user may specify various predefined paradigms to analyze, and may specify various weights or preferences to assigned to the predefined paradigms.

At block 420, the machine learning process identifies which attributes that, when varied, have the greatest effect on the output of recommended action plans from the diagnosis paradigms. For example, a first paradigm may use a set of several attributes to determine and rank various action plans, and the machine learning process identifies which of those attributes, whether used alone or in combination with other attributes, affect the ranking or output of the first paradigm. The machine learning process may identify one attribute as having a significant effect under one paradigm, and not having a significant effect under another paradigm. The machine learning process identifies a subset of the attributes used by the various predefined paradigms that have a greatest effect on the ranking and recommendations. In various embodiments, the number of attributes in the subset is a predefined number or percentage of the total attributes available for analysis (e.g., the top X or X % of analyzes attributes) or may be any attribute whose significance exceeds a predefined threshold.

At block 430, the recommendation application 162 identifies, via a machine learning process, user preferences from historic data. In various embodiments, the user is an individual, a group of individuals, or an institution. The machine learning process analyzes a corpus 172 of historic data to identify the frequency at which a user has selected action plans recommended by various paradigms in the past and the attribute values input for the various paradigms. The frequency of selection is used to weight how the determinations from the paradigms are used. The machine learning model identifies which paradigms are followed under which circumstances (e.g., the user selects the action plans according to paradigm X and under attribute value set A, and selects the action plans according to paradigm Y under attribute value set B).

At block 440, the recommendation application 162 generates the synthetic logical structure to accept values from the identified subset of attributes. The outputs of the synthetic logical structure are based on outputs of the predefined paradigms and may represent an average or consensus recommendation from the several predefined paradigms analyzed, a selective combinations of predefined paradigms (e.g., follow paradigm X in certain cases, but follow paradigm Y in other cases), or a reduced-attribute model of a single paradigm. The synthetic logical structure may indicate placeholder values for attributes not included in the subset that are fed into the predefined paradigms on receipt of various attribute inputs from a user so that the recommendation application 162 may refrain from requesting values for those attributes used by other paradigms but not included in the subset of attributes used by the synthetic paradigm.

Method 400 may then conclude.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. A method comprising:
    identifying a plurality of predefined diagnosis paradigms that identify candidate action plans to treat a plurality of conditions, wherein each predefined diagnosis paradigm includes a logical structure that evaluates which conditions of the plurality of conditions to treat by which of the candidate action plans based on attribute inputs;
    creating a synthetic diagnosis paradigm via a machine learning process based on prior selections of the candidate action plans from the plurality of predefined diagnosis paradigms and values entered for the attribute inputs on the prior selections of the candidate action plans, wherein the synthetic diagnosis paradigm identifies the candidate action plans to treat the plurality of conditions based on a subset of the attribute inputs used by the plurality of predefined diagnosis paradigms and includes a synthetic logical structure that evaluates which conditions of the plurality of conditions to treat, wherein the synthetic diagnosis paradigm and the plurality of predefined diagnosis paradigms comprise a paradigm set;
    generating a graphical user interface (GUI) to prompt input for values for the subset of attribute inputs;
    in response to receiving the values for the subset of attribute inputs, identifying at least one condition of the plurality of conditions according to the paradigm set; and
    displaying the candidate action plans in the GUI in association with the paradigm set according to evaluations of the candidate action plans based on respective logical structures for the paradigm set, wherein the GUI highlights a preferred candidate action plan for each respective diagnosis paradigm of the paradigm set, wherein the candidate action plans are displayed simultaneously with one another in the GUI as individually selectable elements; and
    in response to receiving a positive selection in the GUI of a given candidate action plan associated with one selected diagnosis paradigm of the paradigm set that is not the preferred candidate action plan for the selected diagnosis paradigm, but is the preferred candidate action plan for a different one of the paradigm set, prompting, in the GUI, for input for additional values for the attribute inputs not included in the subset.

2. The method of claim 1, wherein displaying the candidate action plans in the GUI further comprises:
    generating a ranking of the paradigm set based on frequencies of prior selections of candidate action plans from each respective diagnosis paradigm; and
    ordering display of the respective diagnosis paradigms in the GUI based on the ranking.

3. The method of claim 1, further comprising:
in response to receiving the additional values, updating the GUI based on the additional values.

4. The method of claim 1, further comprising:
receiving a second selection of a second given candidate action plan from a given diagnosis paradigm that uses additional attribute inputs from those included in the subset of attribute inputs; and
refraining from prompting for entry of any of the additional attribute inputs.

5. The method of claim 1, wherein particular attribute inputs comprising the subset of attribute inputs are selected from the plurality of predefined diagnosis paradigms based on an impact ranking of the particular attribute inputs to differentiate between conditions of the plurality of conditions.

6. The method of claim 1, further comprising:
in response to receiving a second positive selection in the GUI of a second candidate action plan associated with a second selected diagnosis paradigm selected from the paradigm set, wherein the second candidate action plan is the preferred candidate action plan for the selected second diagnosis paradigm, accepting the second positive selection and refraining from prompting for additional input from a user.

7. The method of claim 1, wherein the input prompting for the additional values for the attribute inputs not included in the subset requests a reason why the given candidate action plan was selected in association with the selected diagnosis paradigm instead of in association with the different one diagnosis paradigm for which the candidate action plan is the preferred candidate action plan.

8. A system comprising:
a processor; and
a memory storage device including instructions that when performed by the processor cause the system to:
identify a plurality of predefined diagnosis paradigms that identify candidate action plans to treat a plurality of conditions, wherein each predefined diagnosis paradigm includes a logical structure that evaluates which conditions of the plurality of conditions to treat by which of the candidate action plans based on attribute inputs;
create a synthetic diagnosis paradigm via a machine learning process based on prior selections of the candidate action plans from the plurality of predefined diagnosis paradigms and values entered for the attribute inputs on the prior selections of the candidate action plans, wherein the synthetic diagnosis paradigm identifies the candidate action plans to treat the plurality of conditions based on a subset of the attribute inputs used by the plurality of predefined diagnosis paradigms and includes a synthetic logical structure that evaluates which conditions of the plurality of conditions to treat, wherein the synthetic diagnosis paradigm and the plurality of predefined diagnosis paradigms comprise a paradigm set;
generate a graphical user interface (GUI) to prompt input for values for the subset of attribute inputs;
in response to receiving the values for the subset of attribute inputs, identify at least one condition of the plurality of conditions according to the paradigm set; and
display the candidate action plans in the GUI in association with the paradigm set according to evaluations of the candidate action plans based on respective logical structures for the paradigm set, wherein the GUI highlights a preferred candidate action plan for each respective diagnosis paradigm of the plurality of predefined diagnosis paradigms and the synthetic diagnosis paradigm wherein the candidate action plans are displayed simultaneously with one another in the GUI as individually selectable elements; and
in response to receiving a positive selection in the GUI of a given candidate action plan associated with one selected diagnosis paradigm of the paradigm set that is not the preferred candidate action plan for the selected diagnosis paradigm, but is the preferred candidate action plan for a different one of the paradigm set, prompt, in the GUI, for input for additional values for the attribute inputs not included in the subset.

9. The system of claim 8, wherein to display the candidate action plans in the GUI, the instructions further cause the system to:
generate a ranking of the paradigm set based on frequencies of prior selections of candidate action plans from each respective diagnosis paradigm; and
order display of the respective diagnosis paradigms in the GUI based on the ranking.

10. The system of claim 8, wherein the instructions further cause the system to:
in response to receiving the additional values, update the GUI based on the additional values.

11. The system of claim 8, wherein the instructions further cause the system to:
receive a second selection of a second given candidate action plan from a given diagnosis paradigm that uses additional attribute inputs from those included in the subset of attribute inputs; and
refrain from prompting for entry of any of the additional attribute inputs.

12. The system of claim 8, wherein particular attribute inputs comprising the subset of attribute inputs are selected from the plurality of diagnosis paradigms based on an impact ranking of the particular attribute inputs to differentiate between conditions of the plurality of conditions.

13. The system of claim 8, wherein the instructions further cause the system to:
in response to receiving a second positive selection in the GUI of a second candidate action plan associated with a second selected diagnosis paradigm selected from the paradigm set, wherein the second candidate action plan is the preferred candidate action plan for the selected second diagnosis paradigm, accept the second positive selection and refrain from prompting for additional input from a user.

14. The system of claim 8, wherein the input prompting for the additional values for the attribute inputs not included in the subset requests a reason why the given candidate action plan was selected in association with the selected diagnosis paradigm instead of in association with the different one diagnosis paradigm for which the candidate action plan is the preferred candidate action plan.

15. A computer readable storage medium including instructions that when performed by a processor configure the processor to:
identify a plurality of predefined diagnosis paradigms that identify candidate action plans to treat a plurality of conditions, wherein each predefined diagnosis paradigm includes a logical structure that evaluates which conditions of the plurality of conditions to treat by which of the candidate action plans based on attribute inputs;

create a synthetic diagnosis paradigm via a machine learning process based on prior selections of the candidate action plans from the plurality of predefined diagnosis paradigms and values entered for the attribute inputs on the prior selections of the candidate action plans, wherein the synthetic diagnosis paradigm identifies the candidate action plans to treat the plurality of conditions based on a subset of the attribute inputs used by the plurality of predefined diagnosis paradigms and includes a synthetic logical structure that evaluates which conditions of the plurality of conditions to treat, wherein the synthetic diagnosis paradigm and the plurality of predefined diagnosis paradigms comprise a paradigm set;

generate a graphical user interface (GUI) to prompt input for values for the subset of attribute inputs;

in response to receiving the values for the subset of attribute inputs, identify at least one condition of the plurality of conditions according to the paradigm set; and display the candidate action plans in the GUI in association with the paradigm set according to evaluations of the candidate action plans based on respective logical structures for the paradigm set, wherein the GUI highlights a preferred candidate action plan for each respective diagnosis paradigm of the paradigm set, wherein the candidate action plans are displayed simultaneously in the GUI as individually selectable elements; and in response to receiving a positive selection in the GUI of a given candidate action plan associated with one selected diagnosis paradigm of the paradigm set that is not the preferred candidate action plan for the selected diagnosis paradigm, but is the preferred candidate action plan for a different one of the paradigm set, prompt, in the GUI, for input for additional values for the attribute inputs not included in the subset.

16. The computer readable storage medium of claim 15, wherein the instructions further configure the processor to:
in response to receiving the additional values, update the GUI based on the additional values.

17. The computer readable storage medium of claim 15, the instructions further configure the processor to:
receive a second selection of a second given candidate action plan from a given diagnosis paradigm that uses additional attribute inputs from those included in the subset of attribute inputs; and
refrain from prompting for entry of any of the additional attribute inputs.

18. The computer readable storage medium of claim 15, wherein particular attribute inputs comprising the subset of attribute inputs are selected from the plurality of diagnosis paradigms based on an impact ranking of the particular attribute inputs to differentiate between conditions of the plurality of conditions.

19. The computer readable storage medium of claim 15, wherein the instructions further configure the processor to:
in response to receiving a second positive selection in the GUI of a second candidate action plan associated with a second selected diagnosis paradigm selected from the paradigm set, wherein the second candidate action plan is the preferred candidate action plan for the selected second diagnosis paradigm, accept the second positive selection and refrain from prompting for additional input from a user.

20. The computer readable storage medium of claim 15, wherein the input prompting for the additional values for the attribute inputs not included in the subset requests a reason why the given candidate action plan was selected in association with the selected diagnosis paradigm instead of in association with the different one diagnosis paradigm for which the candidate action plan is the preferred candidate action plan.

\* \* \* \* \*